(12) United States Patent
Becard et al.

(10) Patent No.: US 8,101,171 B2
(45) Date of Patent: Jan. 24, 2012

(54) MODULATORS OF THE DEVELOPMENT OF MYCHORRIZAL FUNGI WITH ARBUSCULES, AND USES THEREOF

(75) Inventors: Guillaume Becard, Odars (FR); Christophe Roux, Vernet (FR); Nathalie Sejalon-Delmas, Nailloux (FR); Virginie Puech, Toulouse (FR); Sébastien Roy, Balma (FR)

(73) Assignees: Universite Paul Sabatier Toulouse III, Toulouse (FR); Centre National de la Recherche Scientifique (C.N.R.S.), Paris (FR)

( * ) Notice: Subject to any disclaimer, the term of this patent is extended or adjusted under 35 U.S.C. 154(b) by 1538 days.

(21) Appl. No.: 10/588,767

(22) PCT Filed: Feb. 9, 2005

(86) PCT No.: PCT/FR2005/000284
§ 371 (c)(1),
(2), (4) Date: Aug. 8, 2006

(87) PCT Pub. No.: WO2005/077177
PCT Pub. Date: Aug. 25, 2005

(65) Prior Publication Data
US 2008/0318773 A1 Dec. 25, 2008

(30) Foreign Application Priority Data
Feb. 10, 2004 (FR) ..................... 04 01282

(51) Int. Cl.
*A01N 63/00* (2006.01)
*A01N 63/04* (2006.01)
*A01N 65/00* (2009.01)
*A01N 43/16* (2006.01)
*C07D 311/22* (2006.01)

(52) U.S. Cl. .............................. 424/93.5; 549/403; 71/88

(58) Field of Classification Search ........................ None
See application file for complete search history.

(56) References Cited

U.S. PATENT DOCUMENTS
5,002,603 A * 3/1991 Safir et al. ..................... 504/100

FOREIGN PATENT DOCUMENTS
WO 91/07868 6/1991
WO 97/28150 8/1997

OTHER PUBLICATIONS

Becard et al. Fungal growth stimulation of CO2 and root exudates of besicular-arbuscular mycorrhyizal symbiosis. (1989) Applied and Environmental Microbiology; vol. 55; pp. 2320-2325.*

Elias et al. Hyphal elongation of glumus fasciculatus in response to root exudates. (1987) Applied and Environmental Microbiology ; vol. 53; pp. 1928-1933.*

Yokota et al. Alectrol and orobanchol, germination stimulants for orobanche minor, from its host red clover. (1993) Phytochemistry; vol. 49; 99. 1967-1973.*

Gianinazzi-Pearson et al. In Vitro Enhancement of Spore Germination and Early Hyphal Growth of a Vesicular-Arbuscular Mycorrhizal Fungus by Host Root Exudates and Plant Flavonoids. Symbiosis, 7 (1989) 243-255.*

Nagahashi et al. Partial separation of root exudate components and their effects upon the growth of germinated spores of AM fungi. Mycol. Res. 104 (12) 1453-1464. Dec. 2000.*

Becard G. and Piche Y. : "Fungal Growth stimulation by CO2 and Roots exudates in Vescicular-Arbuscular Mycorrhizial Symbiosis" Applied and Environmental Microbiology, vol. 55, No. 9, Sep. 1989, pp. 2320-2325, XP009036591.

Elias K. S. and Safir, G. R. : Applied and Environmental Microbiolog, vol. 53, No. 8, Aug. 1987, pp. 1928-1933, XP009036589.

Nefkens Gerard H L et al: "Synthesis of a phthaloylglycine-derived strigol analogue and its germination stimulatory activity toward seeds fo the parasitic weeks *Striga hermonthica* and *Orobanche crenata*" Journal of Agricultural and Food Chemistry vol. 45, No. 6, 1997, pp. 2273-2277, XP002296378.

Yokota Takao et al: "Alectrol and orobanchol, germination stimulants for *Orobanche minor*, from iots host red clover" Phytochemistry (Oxford), vol. 49, No. 7, Dec. 1998, pp. 1967-1973, XP002296379.

Schussler A. et al. : "A new fungal phylum, the Glomeromycota: phylogeny and evolution *" Mycological Research, 2001, 105:1413-1421.

Walker et al.: "Root Exudation and Rhizosphere Biology [1]" Plant Physiology, 2003, 132: 44-51.

Cook et al. : Science, 1966, 1954: 1189-1190.

Cook et al.: Journal of the American Chemical Society , 1972, 94:6198-6911.

Johnson et al., "A novel approach to *Striga* and *Orobanche* control using synthetic germination stimulants" Weed Research, 1976, 16:223-227.

Mangnus et al., J. Agric. Food Chem. 1992, 40(6):697-700.
Mangnus et al., J. Agric. Food Chem. 1992, 40(7):1230-1235.
Thuring et al., J. Agric. Food Chem., 1997, 45(6):2278-2283.
Buee M. et al., MPMI, vol. 13, No. 6, 2000, pp. 693-698.
Vierheling et al.: Applied and Environmental Microbiology, Dec. 1998, p. 5004-5007.

* cited by examiner

*Primary Examiner* — Annette Para
(74) *Attorney, Agent, or Firm* — Young & Thompson

(57) ABSTRACT

The identification of compounds, strigolactones, having the ability to stimulate the growth and/or development of arbuscular mycorrhizal fungi (AM fungi). Such compounds are, for example, the natural strigolactones strigol, alectrol, sorgolactone, orobanchol, or their synthetic analogs GR7, GR24, Nijmegen-1, demethylsorgolactone. New ways of developing an agriculture that is more respectful of the environment, and permits the implementation, on a small or large scale, of advanced mycorrhization techniques aimed at optimizing the production of fungic inoculum, the use of AM fungi in soils or cultivation substrates, and intensifying the symbiotic interaction between these microorganisms and cultivated plants.

23 Claims, No Drawings

MODULATORS OF THE DEVELOPMENT OF MYCHORRIZAL FUNGI WITH ARBUSCULES, AND USES THEREOF

The invention relates to the cultivation of terrestrial plants and of arbuscular mycorrhizal fungi. It relates more particularly to the techniques used to stimulate the growth and development of arbuscular mycorrhizal fungi and/or to stimulate the mycorrhization and development of plants that are valuable in agronomy and/or forestry.

A large number of terrestrial plants, from the juvenile stage, live in symbiosis with microorganisms which are associated with them at root level. Among such microorganisms, arbuscular mycorrhizal fungi (AM fungi), which are also known as "vesicular-arbuscular fungi" (VAM fungi), establish with certain plants, known as host plants, an intimate interaction which ensures the mutualistic functioning of the symbiosis. The establishment of such a symbiosis between a plant and mycorrhizal fungi is called mycorrhization.

AM fungi form part of a group of archaic fungi, the Glomeromycota, whose ancestors would be the origin of the modern groups Ascomycota and Basidiomycota (Schussler et al., Mycological Research, 2001, 105:1413-1421).

The ancestors of the Glomeromycota, which were certainly present when the first terrestrial plants appeared, would have contributed to the acclimatization of the plants to the terrestrial medium, providing the plants with a more efficient supply of water and mineral salts. By co-evolution (evolutive bio-radiations), the AM fungi, as they evolved, would have acquired the ability to interact with an increasing number of plants, known as host plants. It is currently estimated that more than 80% of terrestrial plant species are associated with arbuscular mycorrhizal fungi, including herbaceous species of major economic interest (both cereal and fruit species as well as vegetable species), but also ligneous (ornamental, forest and fruit) species.

At the level of the fungus, this interaction manifests itself in the appearance of filamentous structures, called hyphae, which spread to form an entire network in the ground. The totality of the hyphae of the fungus forms the mycelium, which corresponds to the assimilative structure of the fungus.

At the same time, the fungus also develops in the roots of the host plant. There is therefore a fungic continuum between the ground and the root tissues. Thanks to the extraradical mycelial network of the fungus, the host plant has available a larger volume of soil to explore in order to acquire water and mineral salts for itself. In addition to the improved supply of water and minerals from which the host plant benefits, this symbiotic association would also improve its resistance to root pathologies.

This functional alliance is also beneficial for the AM fungi, which are only able to live in association with roots, on which they depend for their supply of carbon-containing substrates. Accordingly, being physically and functionally associated with the host plant, these microorganisms multiply in the ground by dissemination of propagules (spores and/or mycelium).

For several years, attempts have been made to develop controlled symbiosis techniques allowing the beneficial interaction between AM fungi and numerous cultivated plant species, of agriculture and forestry, to be intensified so as to improve the supply of water and minerals to those host plants as well as their resistance to root diseases. Such controlled symbiosis techniques will open up promising perspectives for the development of cultivation practices which are more respectful of the environment.

In particular, the spreading of AM fungi on cultivation soils would optimize their content of these microorganisms that are beneficial to the plant to be cultivated, and would consequently permit a substantial reduction in the quantities of fertilizers, especially chemical fertilizers, ordinarily employed to enrich the soils, in particular phosphates and nitrates, which contribute greatly to the pollution of the phreatic nappes.

However, in order for such a concept to be usable in large crops, it would be necessary to have available a considerable quantity of such AM fungi, preferably in the form of spores, which are easier to handle and store. At present, however, there is unfortunately no known method that is capable of producing spores of AM fungi in a quantity sufficient for such an application.

Numerous techniques have been proposed, however, for improving the development and growth of AM fungi, especially for enhancing their sporulation. Such techniques, which are generally based on a co-culture of the fungus in the presence of a whole host plant in a pot, or in vitro in the presence only of cultivated roots, have to date only resulted in the production of propagules in relatively small quantities, which are insufficient for a large-scale agronomic application.

Supplementing the co-culture medium with root exudates, which are said to be stimulators of the development of AM fungi, has also been envisaged (Bécard et al., Appl. Environ. Microbiol., 1989, 55:2320-25; Elias et al., Appl. Environ. Microbiol., 1987, 53:1928-33). Unfortunately, no method is available at present for obtaining such stimulators other than the "passive" and slow recovery of the exudates gradually produced and secreted by the roots of the plants. Equally, the quantities so collected are only just sufficient for laboratory experiments.

Owing to the great complexity of the composition of these exudates, which contain thousands of molecules ranging from simple sugars, which are present in large concentrations, to much more complex molecules, which are present as traces (see especially Walker et al., Plant Physiology, 2003, 132:44-51), and despite the very large number of works which have already been carried out on this subject, the factor(s) actually involved in stimulating the development and growth of AM fungi has (have) still not been identified.

Within this context, the invention aims to propose novel factors for stimulating the development and/or growth of AM fungi in order to remedy the very poor availability of these organisms.

It is also a main object of the invention to propose such stimulation factors, the availability and accessibility of some of which do not constitute a limitation as regards their large-scale application, that is to say an application which goes beyond laboratory bench tops or simple cultivation in a greenhouse.

In particular, the invention aims to improve the productivity of the methods for obtaining AM fungus inoculum, especially on an industrial scale.

Throughout the text, "inoculum" is understood as meaning any form of AM fungus that is capable of colonizing a host plant: spores, hyphae, vesicles, mycorrhizated root fragments.

In fine, the invention aims to improve the methods for the mycorrhization of plants, especially of plants that are valuable in agronomy or forestry, for intensive cultivation that is more respectful of the environment.

Accordingly, the invention relates to a method of treating arbuscular mycorrhizal fungi, known as AM fungi—especially in the form of spores—in which the AM fungi are brought into contact with at least one stimulating agent in at least an amount that is suitable for stimulating the development and/or growth of said AM fungi, said stimulating agent having a structure selected from:

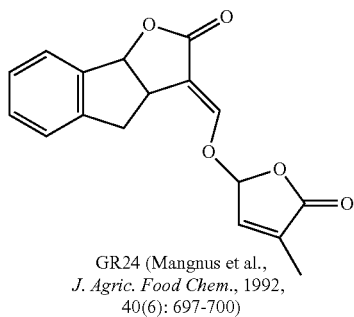

GR24 (Mangnus et al., *J. Agric. Food Chem.*, 1992, 40(6): 697-700)

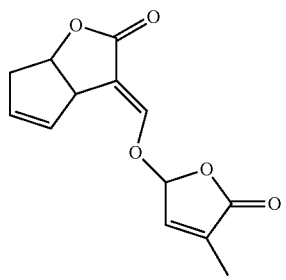

GR7 (Johnson et al., *Weed Res.*, 1976, 16: 223-227)

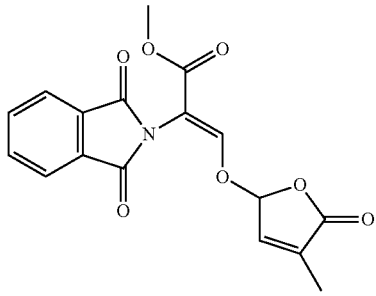

Nijmegen 1 (Nefkens et al., *J. Agric. Food Chem.*, 1997, 45(6): 2273-2277)

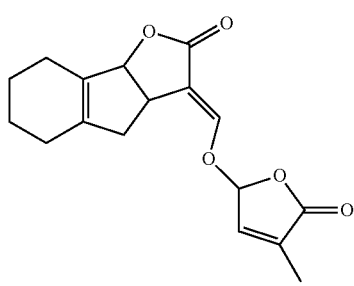

Demethylsorgolactone (Thuring et al., *J. Agric. Food Chem.*, 1997, 45(6): 2278-2283)

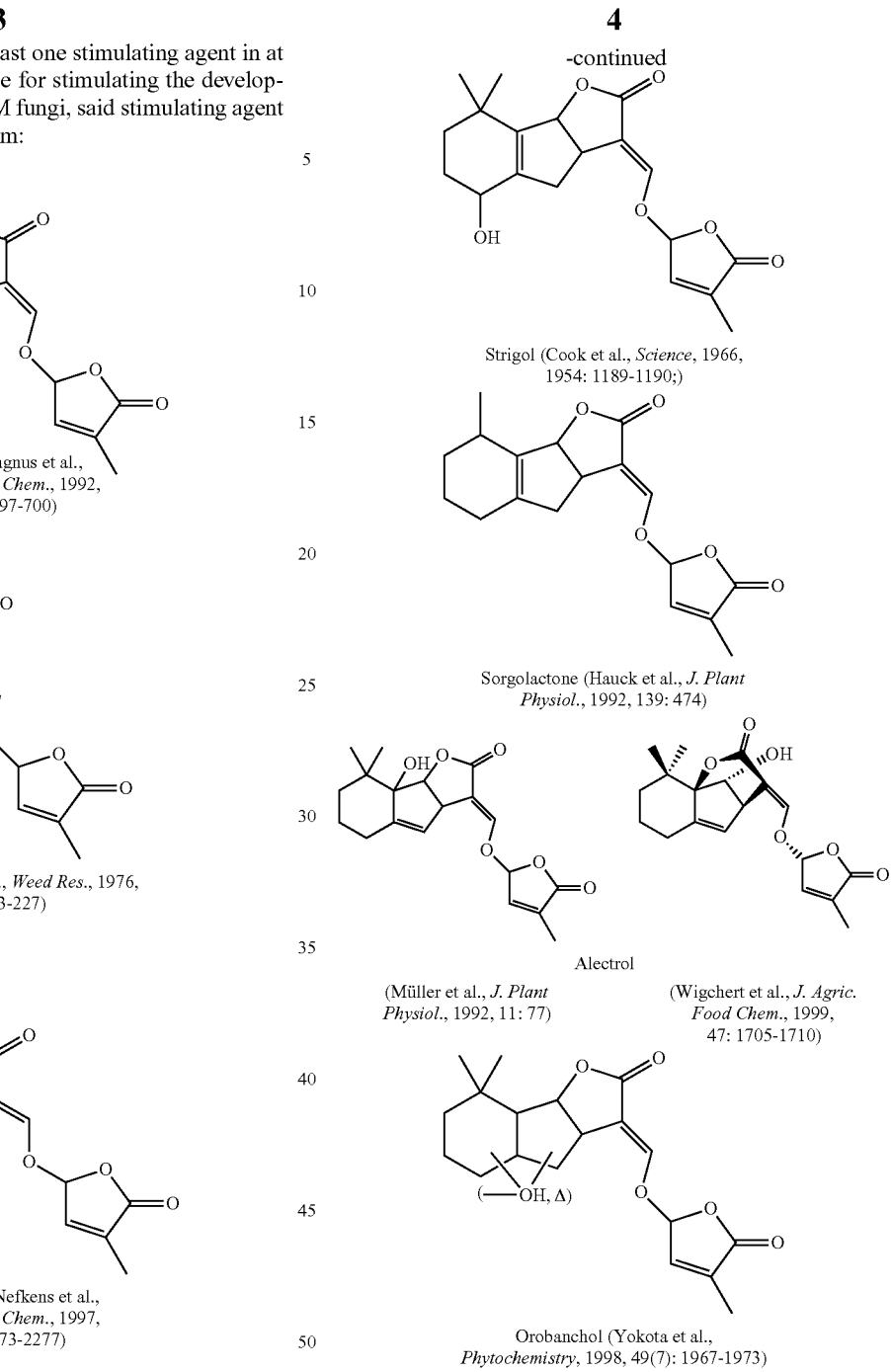

The invention is accordingly based on the identification of compounds of a defined structure having the capacity to stimulate the growth and development of arbuscular mycorrhizal fungi. In particular, the works carried out by the inventors have revealed that molecules which are already known, GR7 and GR24, which are synthetic analogs of natural compounds belonging to the strigolactone family, might advantageously be used for purposes other than the elimination of parasitic plants.

Strigolactones (such as strigol, alectrol, sorgolactone, orobanchol), which are natural compounds extracted from root exudates of various plant species, were originally described as agents inducing the germination of seeds of parasitic plants of the groups *Striga* and *Orobanche* (Cook et al., Science, 1966, 1954:1189-1190; Cook et al., J. Amer. Chem. Soc., 1972, 94:6198-6911) which are particularly harmful to some crops of major economic interest, such as crops of sorghum, maize, sugar cane, beans, etc. With strigolactones, it was possible to envisage suicide germination, a new approach in the struggle against parasitic plants.

Put into concrete form with emergence of synthetic analogs, such as GR7 and GR24, which are easier to obtain than the natural compounds and are therefore more suitable for application on an industrial scale, suicide germination consists in treating agricultural soils, which are likely to be infested with parasitic plants, with synthetic strigolactone analogs, the treatment being carried out at a time when the plant to be cultivated is not yet growing in said soils. By disseminating said synthetic analogs, germination of the dormant seeds of the parasitic plants is induced and the parasitic plants, without a host plant to infest, ultimately die through lack of nutrition (Johnson et al., Weed Research, 1976, 16:223-227).

While GR7 and GR24 have hitherto been devoted specifically and solely to the suicide germination of the seeds of parasitic plants belonging to the groups *Striga* and *Orobanche*, the invention proposes a use, hitherto unthinkable, of these molecules for their unexpected biological effect on AM fungi, microorganisms whose phylogeny is far removed from that of the plants *Striga* and *Orobanche*.

In a hitherto unexpected manner, the inventors have found that GR7 and GR24 induce stimulation of the cell respiration of AM fungus spores and permit amplification of the biological process of branching of the hyphae of those fungi. By treating the spores with GR7 and/or GR24, the inventors accordingly succeeded in stimulating the growth and branching of AM fungi. These two physiological and morphological responses are essential for the establishment of the symbiotic interaction between the AM fungi and their host plants.

These works carried out by the inventors accordingly demonstrate that the stimulating effect of root exudates on the development and growth of AM fungi, shown for the first time in works which go back at least to the beginning of the 1980s, is attributable at least partly to strigolactones, compounds which are present in the root exudates only in an infinitesimal quantity, however. Sorgolactone (the strigolactone of sorghum), for example, has been isolated from root exudates collected from 300,000 sorghum plants, resulting in the purification of 5 µg of purified compounds. The quantities obtained are so small that the chemical structure of sorgolactone could only be defined after chemical synthesis of the compound and comparison of the NMR spectra. For the same reason, it has been possible to characterize only five strigolactones to date.

Accordingly, the invention is based on the principle that molecules having a particular structure and configuration, especially the molecules known by the conventional names GR7 and GR24, can be used as factors for stimulating the development and/or growth of AM fungi.

The choice of factor for stimulating the development and/or growth of AM fungi for carrying out a method for treating AM fungi—especially in the form of spores—according to the invention is not limited only to GR7 and GR24. The choice extends also to strigolactones in general and, in particular, to strigol, alectrol, sorgolactone and orobanchol.

Likewise, and in all probability, the effect found with GR7 and GR24, but also with strigolactones in general, on the AM fungi is due to the particular structure and configuration of the rings denoted B, C and D of these molecules, as shown hereinbelow for the strigol molecule.

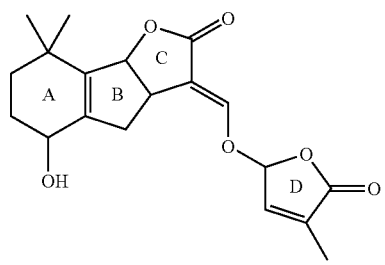

Accordingly, the works of the inventors show that any compound having a structure analogous to GR7, GR24 and to strigolactones, that is to say any compound having the structure of the chain of rings denoted B, C and D of strigolactones (such as, for example, demethylsorgolactone) or simply their configuration (such as, for example, Nijmegen-1, another synthetic strigolactone analog) can be used as an agent for stimulating the development and/or growth of AM fungi, in accordance with the invention.

Advantageously and according to the invention, treatment of the AM fungi, or AM fungus inoculum, is preferably carried out on spores or mycorrhized root fragments.

Advantageously and according to the invention, said treatment is carried out in the presence of living plant material, known as the host plant, corresponding, at least partly, to a constitutive root part of a plant capable of forming a symbiosis with AM fungi.

According to a particular mode of carrying out a method according to the invention, treatment of AM fungi—especially in the form of spores or of mycorrhized root fragments—is carried out in an aseptic medium in vitro.

According to another mode of carrying out a method according to the invention, the treatment is advantageously carried out on cultures of whole host plants cultivated in pots. However, it is also possible to carry out the invention on a larger scale, especially on whole host plants cultivated in the field. In that case there will preferably be used compounds of chemical synthesis, such as GR7 and GR24, which have the advantage, compared with the strigolactones, that they can be available in a sufficient and suitable quantity for industrial application. Some of these compounds, such as GR7 and GR24, are already available commercially and/or can be synthesized according to protocols which are already known (Mangnus et al., J. Agric. Food Chem., 1992, 40(6):697-700; Mangnus et al., J. Agric. Food Chem., 1992, 40(7):1230-1235; Thuring et al., J. Agric. Food Chem., 1997, 45(6):2278-2283).

Advantageously and according to the invention, AM fungi selected from *Glomus intraradices* and *Gigaspora rosea* are used.

The invention extends also to a method of producing AM fungus inoculum. To that end, a co-culture of AM fungi is carried out in the presence of living plant material, known as the host plant, corresponding, at least partly, to a constitutive root part of a plant capable of forming a symbiosis with AM fungi.

In addition and according to the invention, said co-culture is also brought into contact with at least one stimulating agent in at least an amount that is suitable for stimulating the development and/or growth of said AM fungi, said stimulating agent having a structure selected from:

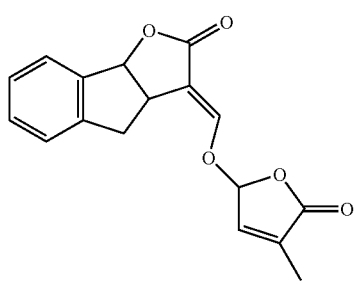

GR24

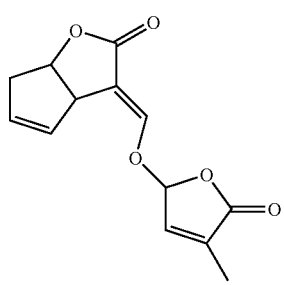

GR7

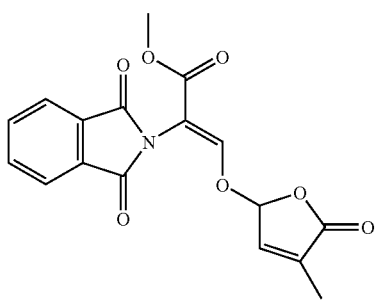

Nijmegen 1

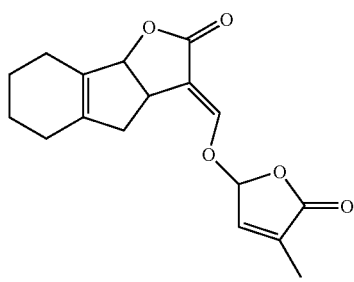

Demethylsorgolactone

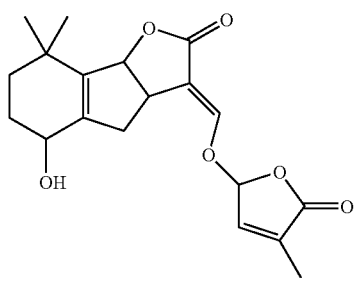

Strigol

-continued

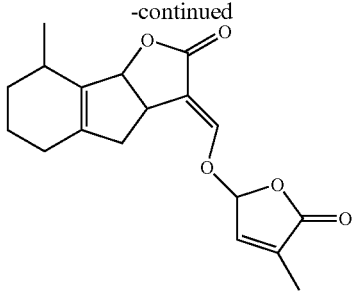

Sorgolactone

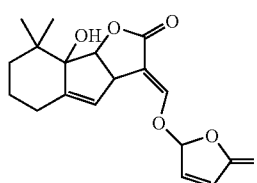 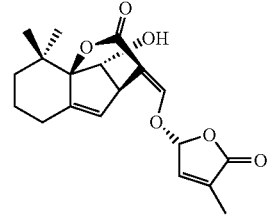

Alectrol

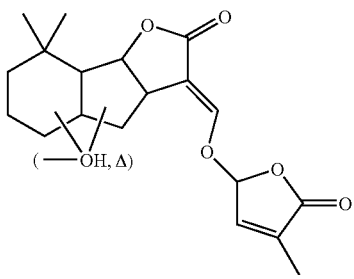

Orobanchol

Advantageously and according to the invention, the AM fungi of said co-culture are treated by a method of treating AM fungi—especially in the form of spores—in accordance with at least one of the procedures described hereinbefore.

More generally, the invention can advantageously fall within the scope of research problems aimed at increasing the natural richness of cultivatable soils in minerals and water, essentially in order to reduce the habitual use of chemical fertilizers, which are often the source of pollution by phosphates and nitrates.

By giving prominence to factors some of which are already available commercially and which are capable of stimulating the development and/or growth of AM fungi, the invention thus makes it possible to carry out, advantageously on a large scale, especially on an industrial scale, mycorrhization techniques which were thought up several years ago but the application of which has, until now, been limited by the poor availability of spores and other forms of inoculum of AM fungi, and by a lack of knowledge about effective and readily accessible stimulating factors.

Accordingly, the invention extends also to a method of cultivating a host plant—in particular a host plant valuable in agronomy or forestry—that is capable of forming a symbiosis with AM fungi. To that end, there is added to the cultivation medium at least one agent for stimulating the development and/or growth of AM fungi, which agent is selected from: GR24, GR7, Nijmegen-1, demethylsorgolactone, strigol, alectrol, sorgolactone, orobanchol and their structural analogs.

According to the invention, the stimulating agent is added at the time of sowing of the seeds of the host plant to be cultivated and/or subsequently to said sowing.

In the case of the transplantation into the ground of young plants obtained previously (for example by propagation, micropropagation, layering, in vitro multiplication, etc.), the stimulating agent is added to the cultivation medium (cultivation soil) at the time of said transplantation.

Advantageously and according to the invention, the host plant is cultivated in the field. It can also be cultivated in a greenhouse.

When the host plant is cultivated in the field, it may be that the soil used naturally contains AM fungi in a sufficient quantity. It is then not necessary to supplement the field further with those microorganisms. However, such supplementation may be found to be necessary, in the form of spores or another form of inoculum of AM fungi.

Advantageously and according to the invention, the soil is supplemented with AM fungus inoculum, especially at the time of sowing, and/or agents for stimulating the development and/or growth of AM fungi are added repeatedly—especially until harvest.

Advantageously and according to the invention, there are used for the cultivation seeds of the host plant which are encapsulated in the above-mentioned stimulating agents by means of a coating of a material suitable for permitting the development of plantlets of said host plant and the release of said stimulating agents, essentially during the first waterings.

The invention extends to a composition comprising, in combination, a quantity of seeds of a host plant capable of forming a symbiosis with AM fungi, and a quantity of agent for stimulating the development and/or growth of AM fungi, which agent is selected from: GR24, GR7, Nijmegen-1, demethylsorgolactone, strigol, alectrol, sorgolactone, orobanchol and structural analogs thereof.

Advantageously and according to the invention, said composition is formulated so as to form a coating by means of a material capable of disintegrating on contact with a solvent, especially water.

Advantageously, a composition according to the invention also comprises a quantity of AM fungi, in particular in the form of spores—especially of *Glomus intraradices* or *Gigaspora rosea*.

The invention extends also to a composition comprising, in combination, a quantity of AM fungus inoculum, in particular spores, and a quantity of agent for stimulating the development and/or growth of AM fungi, which agent is selected from: GR24, GR7, Nijmegen-1, demethylsorgolactone, strigol, alectrol, sorgolactone, orobanchol and structural analogs thereof.

Advantageously and according to the invention, said composition is formulated so as to form a coating by means of a material capable of disintegrating on contact with a solvent, especially water.

The invention relates also to a method of treating AM fungi, to a method of producing AM fungus inoculum, to a method of cultivating a host plant and to a composition, characterized, in combination, by all or some of the features hereinbefore and hereinafter.

Other objects, features and advantages of the invention will also become apparent from reading the description of the following experimental analyses.

ANALYSIS 1

Effect of GR24 on the Activation of the Cell Respiration of *Glomus intraradices*

Polarographic measurements of oxygen consumption were carried out on *Glomus intraradices* spores in germination, in the presence or absence of GR24.

To that end, *Glomus intraradices* spores are germinated in liquid minimal medium, known as medium M (Table 1 below shows the composition thereof), for one week at 30° C. and in an atmosphere enriched with 2% $CO_2$. 400 spores in 1 ml of medium M are used per test.

In order to stimulate the spores, there are added to each test 10 µl of a 30 µM solution of GR24 in acetone (1%), namely a final concentration of GR24 of 0.3 µM. The controls receive 10 µl of acetone (1%).

The oxygen consumption is measured using an oxygen electrode, known as a Clark electrode (Hansatech Ltd, Hardwick Industrial, Norfolk, United Kingdom), inserted into a Plexiglass chamber. The oxygen electrode is connected to a recorder calibrated between 0 and 100% with atmospheric oxygen.

The spores are introduced into the chamber, and the temperature is maintained at 30° C. by means of a circulating water bath. The rates of oxygen consumption are read directly from the recorder. The measurements of oxygen consumption are carried out over 15 minutes, after 4 hours' stimulation (series 1) and after 5½ hours' stimulation (series 2).

TABLE 1

| CONSTITUENTS | Final concentration (mg · l$^{-1}$) |
|---|---|
| $MgSO_4$, $7H_2O$ | 731 |
| $KNO_3$ | 80 |
| KCl | 65 |
| $KH_2PO_4$ | 4.8 |
| $Ca(NO_3)_2$, $4H_2O$ | 288 |
| NaFe-EDTA | 8 |
| KI | 0.75 |
| $MnCl_2$, $4H_2O$ | 6 |
| $ZnSO_4$, $7H_2O$ | 2.65 |
| $H_3BO_3$ | 1.5 |
| $CuSO_4$, $5H_2O$ | 0.13 |
| $Na_2MoO_4$, $2H_2O$ | 0.0024 |
| Glycine | 3 |
| Thiamine-HCl | 0.1 |
| Pyridoxine | 0.1 |
| Nicotinic acid | 0.5 |
| Myoinositol | 50 |
| Medium supplemented with sucrose | 10 g · l$^{-1}$ |

Two independent series of experiments were carried out. For each, the recorded values correspond to the average of 3 tests. The results obtained are recorded in Table 2 below.

The increase in oxygen consumption is expressed as a percentage relative to that of the control, treated with acetone.

TABLE 2

| | % stimulation (average of 3 tests) |
|---|---|
| Series 1 | 29.0 |
| Series 2 | 76.6 |

ANALYSIS 2

Effect of GR7 on the Activation of the Cell Respiration of *Gigaspora rosea*

The experiments carried out by oxygraph under the same conditions as with GR24 show that GR7 is active on the respiration of *Gigaspora rosea* at a final concentration of 0.1 µM, after 5 hours' stimulation.

The control is carried out using 10 µl of methanol/water (v/v) per ml of medium.

Two independent series of experiments were carried out, after 4 hours' stimulation (series 1) and after 5½ hours' stimulation (series 2).

For each, the values recorded correspond to the averages of 3 tests. The results obtained are shown in Table 3 below.

TABLE 3

| | % stimulation (average of 3 tests) |
|---|---|
| Series 1 | 24.0 |
| Series 2 | 33.6 |

ANALYSIS 3

Effect of GR24 on the Stimulation of the Branching of the Hyphae of *Gigaspora rosea*

The stimulated branching of the hyphae (appearance of new apexes) is the test currently employed to evaluate the stimulating activity of various effectors on endomycorrhizal fungi of the genus *Gigaspora*. This phenomenon occurs naturally close to the roots of host plants, as well as under the action of root exudates, and is considered to be a preparatory phase to the establishment of symbiosis (Buée et al., Molecular Plant-Microbe Interaction, 2000, 13:693-698). This increase in branching is the result of stimulation of the fungus metabolism and leads to an increase in the points of contact between the fungus and the roots of the plant. Any increase in the branching of the hyphae of the fungus increases mycorrhization.

Measurements of branching (expressed as the number of apexes appearing after stimulation) of the germinative tubes of *Gigaspora rosea* were carried out in the presence of various concentrations of GR24.

To that end, *Gigaspora rosea* spores are germinated in gelosed medium M (medium M containing 0.4% (w/v) Phytagel®—SIGMA, France) for 5 days at 30° C. and in an atmosphere enriched with 2% $CO_2$. 10 µl of test agents (in concentrations varying from $10^{-8}$ to $10^{-15}$ M) in solution in 50% methanol are then added to the medium by introduction into a well hollowed out in the gelose.

The controls receive the solvent for the test molecules (10 µl of 50% methanol) under the same conditions.

48 hours after treatment, the apexes formed above the stimulation zone are counted. Two series of experiments with GR24, at different concentrations, were carried out. The results are shown in Table 4 below.

TABLE 4

| Concentration of GR24 (M) | Number of spores treated | Number of newly formed apexes | Apex/spore | Stimulation factor |
|---|---|---|---|---|
| Series 1 | | | | |
| Control | 2 | 6 | 3.0 | 1.0 |
| $10^{-15}$ | 4 | 15 | 3.8 | 1.3 |
| $10^{-12}$ | 4 | 36 | 9.0 | 3.0 |
| $10^{-10}$ | 3 | 45 | 15.0 | 5.0 |
| $10^{-8}$ | 4 | 65 | 16.3 | 5.4 |
| Series 2 | | | | |
| Control | 2 | 7 | 3.5 | 1.0 |
| $10^{-15}$ | 2 | 17 | 8.5 | 2.4 |
| $10^{-12}$ | 4 | 34 | 8.5 | 2.4 |
| $10^{-10}$ | 3 | 40 | 13.3 | 3.8 |
| $10^{-8}$ | 1 | 14 | 14.0 | 4.0 |

Submicromolar doses of GR24 result in stimulation of branching by a factor of 5. With doses lower than picomolar, a clear stimulating effect is still observed.

ANALYSIS 4

Effect of GR7 on the Stimulation of the Hypha Branching of *Gigaspora rosea*

*Gigaspora rosea* spores are germinated in gelosed medium M for 5 days at 30° C. and in an atmosphere enriched with 2% $CO_2$. 10 µl of test agent solution are then added to the medium by introduction into a well hollowed out in the gelose, starting from a solution having a concentration of test agent varying from $10^{-5}$ to $10^{-11}$ M. The controls receive only the solvent for the test agents (10 µl of 50% methanol) under the same conditions.

The apexes formed are counted after 48 hours' treatment. In addition, the elongation activity is evaluated by measuring the number of cm formed before and after treatment. Two series of experiments, with different concentrations of GR7, were carried out. The results obtained are shown in Table 5 below.

TABLE 5

| Concentration of GR7 (M) | Number of spores treated | Number of newly formed apexes | Branching stimulation ratio | cm newly formed/spore | Growth stimulation ratio |
|---|---|---|---|---|---|
| Series 1 | | | | | |
| Control | 4 | 1.75 | | 1.1 | 1.00 |
| $10^{-11}$ | 6 | 5.16 | 2.94 | 2.65 | 2.41 |
| $10^{-9}$ | 5 | 8 | 4.57 | 2.62 | 2.38 |
| $10^{-7}$ | 4 | 8.75 | 5 | 4.65 | 4.23 |
| $10^{-5}$ | 6 | 9.3 | 5.31 | 4.88 | 4.44 |
| Series 2 | | | | | |
| Control | 6 | 2.16 | | 2.49 | 1.00 |
| $10^{-11}$ | 3 | 2.66 | 1.23 | 2.23 | 0.89 |
| $10^{-9}$ | 6 | 6.16 | 2.85 | 4.99 | 2.00 |
| $10^{-7}$ | 7 | 10.42 | 4.82 | 5.09 | 2.04 |
| $10^{-5}$ | 4 | 14.25 | 6.59 | 6.5 | 2.60 |

It is noted that doses of GR7 of the nanomolar order are significantly active on branching (number of newly formed apexes) and on cell elongation.

ANALYSIS 5

Effect of GR7 on the Mycorrhization of *Medicago truncatula* by *Gigaspora rosea*

Measurements of the number of points of contact established between the fungus and the roots during in vitro mycorrhization experiments were carried out. *Medicago truncatula* plants were cultivated in vitro in the presence of *Gigaspora rosea* spores, on medium M enriched with GR7.

For the tests, medium M prepared as above is enriched with GR7 to give a final concentration of 0.1 µM. The controls are carried out with medium M to which methanol is added to give a final concentration of 0.1%. The medium is poured into square Petri dishes (100×100). Three control dishes and three test dishes are prepared. The *Gigaspora rosea* spores are pre-germinated in those dishes (25 per dish) in an oven at 30° C., with 2% $CO_2$, for 6 days. The *Medicago truncatula* seeds are sterilized with Javel water at 8 degrees chlorimetric for 5 minutes. After rinsing with sterile distilled water, they are germinated on a medium composed of bacteriological agar with 1 μM gibberellin. After 24 hours at 4° C., they are transferred into a chamber at 25° C. for 24 hours. Eighteen plantlets so prepared are then distributed randomly in the six experimental dishes containing the spores in the process of germinating. The dishes are placed vertically in a culture chamber (22° C., photoperiod 16 h/8 h) for 3 weeks. The plantlets are harvested and the root systems are stained with ink according to the protocol of Vierheilig (Vierheilig et al., Appl. Environ. Microbiol., 1998, 64:5004-5007).

The number of points of contact established between the fungus and the roots is counted plant by plant after observation under a microscope.

The results obtained are shown in Table 6 below:

TABLE 6

|  | Number of plants | Average points of contact | SEM |
|---|---|---|---|
| Control (methanol) | 10 | 2.2 | 0.8 |
| Test (GR7) | 8 | 7.75* | 2.11 |

*significantly different average (P = 0.02, Mann-Whitney test)

The invention claimed is:

1. A method of treating arbuscular mycorrhiza (AM) fungi, comprising contacting said AM fungi with a composition comprising at least one isolated or purified stimulating agent in at least an amount that is suitable for stimulating the development and/or growth of said AM fungi, said stimulating agent having a structure selected from:

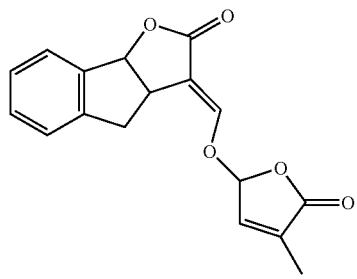

GR24

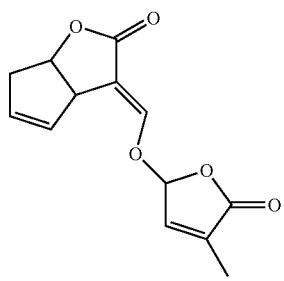

GR7

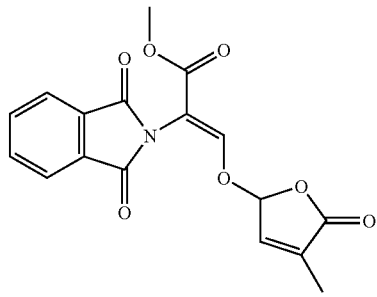

Nijmegen 1

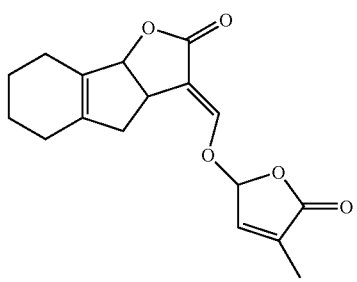

Demethylsorgolactone

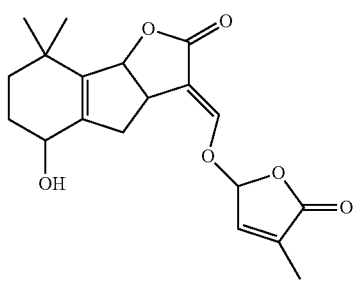

Strigol

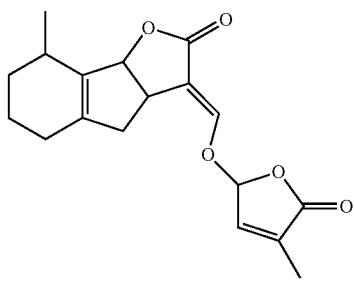

Sorgolactone

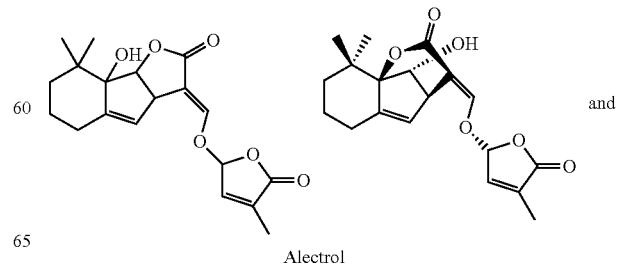

Alectrol and

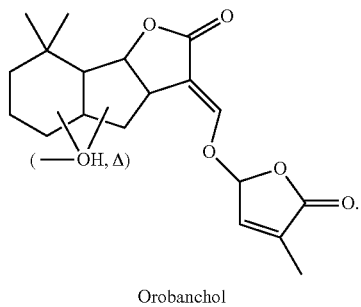

Orobanchol

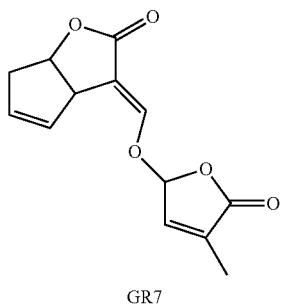

GR7

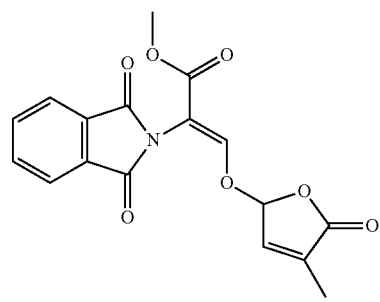

Nijmegen 1

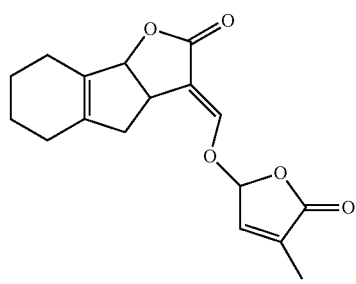

Demethylsorgolactone

2. The method as claimed in claim 1, wherein said method is carried out on AM fungi in the form of spores.

3. The method as claimed in claim 1, wherein said method is carried out on mycorrhizated root fragments.

4. The method as claimed in claim 1, wherein said treatment of the AM fungi is carried out in the presence of living host plant material, corresponding, at least partly, to a constitutive root part of a plant capable of forming a symbiosis with AM fungi.

5. The method as claimed in claim 1, wherein said treatment is carried out in an aseptic medium in vitro.

6. The method as claimed in claim 1, wherein said treatment is carried out on at least one whole host plant cultivated in a pot.

7. The method as claimed in claim 1, wherein said treatment is carried out on at least one whole host plant cultivated in the field.

8. The method as claimed in claim 1, wherein said AM fungi is selected from *Glomus intraradices* and *Gigaspora rosea*.

9. A method of producing inoculum of arbuscular mycorrhizal (AM) fungi, comprising preparing a co-culture of AM fungi in the presence of living host plant material, corresponding, at least partly, to a constitutive root part of a plant capable of forming a symbiosis with AM fungi, and bringing said co-culture into contact with a composition comprising at least one isolated or purified stimulating agent in at least an amount that is suitable for stimulating the development and/or growth of said AM fungi, said stimulating agent having a structure selected from:

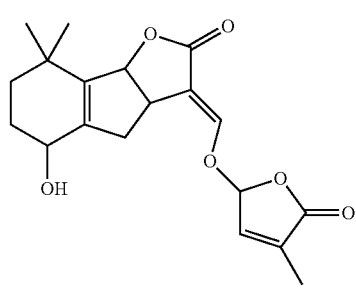

Strigol

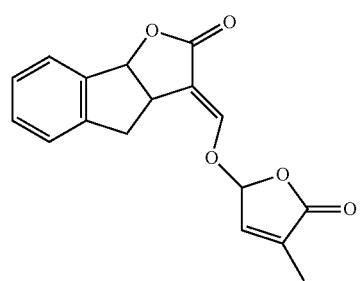

GR24

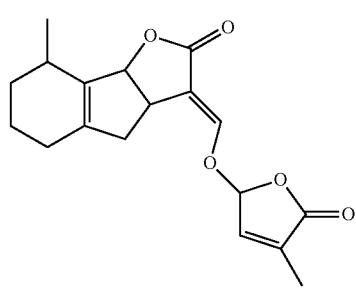

Sorgolactone

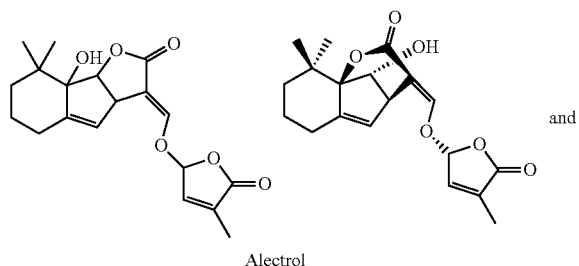

Alectrol

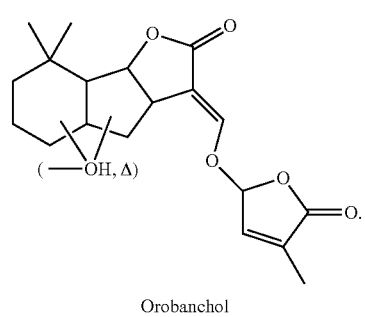

Orobanchol

10. The method as claimed in claim 9, wherein the AM fungi are treated with said co-culture.

11. A method of cultivating a host plant capable of forming a symbiosis with arbuscular mycorrhizal (AM) fungi, comprising adding to a cultivation soil a composition comprising at least one stimulating agent for stimulating the development and/or growth of AM fungi, wherein said stimulating agent is selected from:

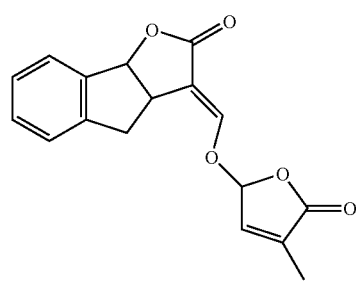

GR24

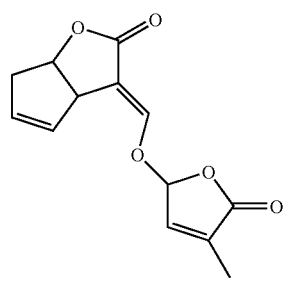

GR27

Nijmegen 1

Demethylsorgolactone

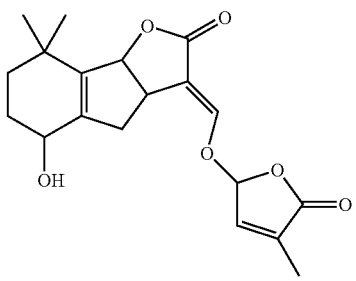

Strigol

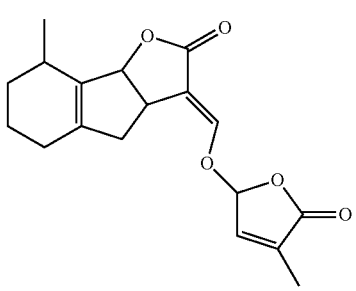

Sorgolactone and

Alectrol

-continued

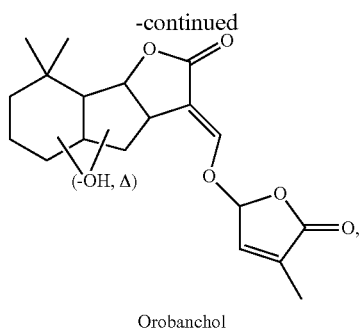

Orobanchol and the stimulating agent is added at the time of sowing of the seeds of the host plant that is to be cultivated and/or subsequently to said sowing.

12. The method as claimed in claim 11, wherein the host plant is cultivated in a greenhouse.

13. The method as claimed in claim 11, wherein the host plant is cultivated in the field.

14. The method according to claim 11, wherein said AM fungi are naturally present in said cultivation soil.

15. The method as claimed in claim 13, wherein said cultivation soil is supplemented with AM fungi.

16. The method as claimed in claim 11, wherein said stimulating agents are added repeatedly.

17. A composition comprising, in combination, a quantity of seeds of a host plant capable of forming a symbiosis with AM fungi, and a quantity of isolated or purified stimulating agent for stimulating the development and/or growth of AM fungi, wherein said stimulating agent is selected from: GR24, GR7, Nijmegen-1, demethylsorgolactone, strigol, alectrol, sorgolactone, and orobanchol.

18. The composition as claimed in claim 17, wherein said composition is formulated so as to form a coating by means of a material capable of disintegrating on contact with a solvent.

19. The composition as claimed in claim 17, further comprising a quantity of AM fungus inoculum.

20. The composition as claimed in claim 19, wherein the AM fungus inoculum is inoculum of AM fungi selected from: *Glomus intraradices* and *Gigaspora rosea*.

21. A composition comprising, in combination, a quantity of AM fungus inoculum and a quantity of stimulating agent for isolated or purified stimulating the development and/or growth of AM fungi, wherein the stimulating agent is selected from: GR24, GR7, Nijmegen-1, demethylsorgolactone, strigol, alectrol, sorgolactone, and orobanchol.

22. The composition as claimed in claim 21, wherein said composition is formulated so as to form a coating by means of a material capable of disintegrating on contact with a solvent.

23. The method as claimed in claim 1, wherein the stimulating agent is GR24 or GR7.

* * * * *